(12) United States Patent
Biedermann et al.

(10) Patent No.: US 11,224,462 B2
(45) Date of Patent: Jan. 18, 2022

(54) COUPLING DEVICE, IN PARTICULAR FOR USE IN ORTHOPEDIC SURGERY

(71) Applicant: BIEDERMANN TECHNOLOGIES GMBH & CO. KG, Donaueschingen (DE)

(72) Inventors: Timo Biedermann, Trossingen (DE); Achim Schünemann, Mühlhausen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 84 days.

(21) Appl. No.: 16/700,502

(22) Filed: Dec. 2, 2019

(65) Prior Publication Data
US 2020/0179008 A1    Jun. 11, 2020

Related U.S. Application Data

(60) Provisional application No. 62/775,580, filed on Dec. 5, 2018.

(30) Foreign Application Priority Data

Dec. 5, 2018 (EP) .................................. 18 210 576

(51) Int. Cl.
*A61B 17/64* (2006.01)
*A61B 17/70* (2006.01)

(52) U.S. Cl.
CPC ........ *A61B 17/645* (2013.01); *A61B 17/7001* (2013.01); *A61B 17/7052* (2013.01)

(58) Field of Classification Search
CPC .............. A61B 17/7002; A61B 17/708; A61B 17/7077; A61B 17/7035; A61B 17/7023;
(Continued)

(56) References Cited

U.S. PATENT DOCUMENTS 4,771,767 A * 9/1988 Steffee ............... A61B 17/7002
606/256
7,195,632 B2   3/2007 Biedermann et al.
(Continued)

FOREIGN PATENT DOCUMENTS

DE    8712943 U1   11/1987
DE    3807335 A1    9/1989
(Continued)

OTHER PUBLICATIONS

Extended European Search Report for Application No. 18210576.7, dated Jun. 24, 2019, 8 pages.

*Primary Examiner* — Pedro Philogene
(74) *Attorney, Agent, or Firm* — Lewis Roca Rothgerber Christie LLP (57) ABSTRACT

A coupling device includes a first coupling body configured to be coupled to a first bone anchor, a second coupling body configured to be coupled a second bone anchor, and a connection device comprising a first connection member connectable to the first coupling body, a second connection member connectable to the second coupling body, and a length adjustment member positionable between and insertable at least partially into each of the first and second connection members. The first and second connection members are movable relative to the length adjustment member. The length adjustment member can be actuated in a first direction to increase a distance between the first connection member and the second connection member, and in a second direction different from the first direction to decrease the distance between the first connection member and the second connection member.

22 Claims, 6 Drawing Sheets (58) Field of Classification Search
CPC ............ A61B 17/7025; A61B 17/7049; A61B 17/645; A61B 17/7001; A61B 17/7004; A61B 17/7007; A61B 17/7052
See application file for complete search history.

(56) References Cited

U.S. PATENT DOCUMENTS

| | | | |
|---|---|---|---|
| 9,198,696 B1* | 12/2015 | Bannigan | ............ A61B 17/7052 |
| 10,098,665 B2 | 10/2018 | Rutschmann et al. | |
| 2011/0172714 A1* | 7/2011 | Boachie-Adjei | ... A61B 17/7076 606/264 |

FOREIGN PATENT DOCUMENTS

| | | |
|---|---|---|
| DE | 9112466 U1 | 12/1991 |
| WO | WO 2012/034005 A2 | 3/2012 |

\* cited by examiner

COUPLING DEVICE, IN PARTICULAR FOR USE IN ORTHOPEDIC SURGERY

CROSS-REFERENCE TO RELATED APPLICATION(S)

The present application claims priority to and the benefit of U.S. Provisional Patent Application No. 62/775,580, filed Dec. 5, 2018, the contents of which are hereby incorporated by reference in their entirety, and claims priority from European Patent Application EP 18 210 576.7, filed Dec. 5, 2018, the contents of which are hereby incorporated by reference in their entirety.

BACKGROUND

Field

The application relates to a coupling device, in particular for use in orthopedic surgery. More specifically, the application is related to a coupling device for the treatment of spinal disorders or for use in trauma surgery.

Description of Related Art

In the treatment of spinal deformities, such as, for example, scoliosis, usually a plurality of screws are placed along the length of a curve in the spine to be corrected, and instruments are used to decrease the curvature. Scoliosis may involve a deformity in the coronal and transverse planes (rotational deformity), as well as in the sagittal plane. Therefore, a rotational correction of a vertebra or a group of vertebrae may become necessary. To accomplish this, extension sleeves may be fixed to pedicle screws placed into the pedicles of a vertebra, and thereafter connected by a coupling device. With the aid of the coupling device, the vertebra may be rotated.

A stabilizer for a spine derotation system is known from U.S. Pat. No. 10,098,665 B2. The stabilizer is configured to join fixture members extending from the same vertebra. It comprises a first and a second end member each defining a cylindrical sleeve including an elongated central opening for receiving the proximal end of corresponding first and second fixture members. A body is provided between the first and second end members and is configured to couple motion of the proximal ends of the fixture members. In one embodiment the body includes two members, one configured to slide within the other to adjust the length of the body. In another example, the body includes two members, one with a shaft with a threaded portion and the other with a tube and a threaded opening configured to receive the threaded portion of the shaft. Further, the system includes a first handle and a second handle, which are used to lock the end members to the respective fixture members.

Another coupling device known from U.S. Pat. No. 7,195,632 is comprised of a connecting element for connecting two rod-shaped elements capable for use for bone or vertebra stabilization. A length of the connecting element can be adjusted during use of the connecting element.

SUMMARY

It is an object of the invention to provide an improved coupling device that is simple and versatile in use.

According to an aspect of the disclosure, a coupling device, in particular for use in orthopedic surgery, includes a first coupling body that is configured to be coupled to a first bone anchor, a second coupling body that is configured to be coupled a second bone anchor, a connection device that is configured to connect the first coupling body and the second coupling body, wherein the connection device includes a first connection member and a second connection member, and wherein a distance between the first and second connection members is adjustable along a connection axis, and a length adjustment member that is configured to be actuated in a first direction to increase the distance between the first connection member and the second connection member, and in a second direction to decrease the distance between the first connection member and the second connection member.

The length adjustment of the coupling device can be easily carried out by actuation of the length adjustment member. Moreover, the length adjustment member can be actuated precisely, so that a precise adjustment of the length of the coupling device is possible. Beyond that, the coupling device is also adjustable with respect to the spatial directions, due to a pivot connection between the connection members and the coupling bodies.

In addition, the coupling device has a space-saving design. The coupling device can be connected with other coupling devices to form an assemblage of coupling devices for performing correction steps, such as rotational correction steps, for several spinal segments simultaneously.

According to another aspect of the disclosure, the coupling device, in particular for use in orthopedic surgery, includes a coupling body configured to be coupled to a bone anchor, a connection member pivotably held in a receiving portion of the coupling body, the connection member being configured to connect directly or indirectly to another coupling body, and a locking member acting directly or indirectly onto the connection member to lock the connection member in one pivot position, wherein the locking member includes an eccentric portion that can assume a first configuration in which the eccentric portion locks the connection member and a second configuration in which the eccentric portion releases the connection member, and wherein the eccentric portion is moved from the first configuration to the second configuration by rotating the locking member.

With the coupling device according to this aspect, a pivot angle between the coupling body and the connection member can be easily locked and released.

According to a still further aspect of the disclosure, the coupling device, in particular for use in orthopedic surgery, includes a coupling body configured to be coupled to a bone anchor, a connection member pivotably held in a receiving portion of the coupling body, the connection member being configured to connect directly or indirectly to another coupling body, wherein the coupling body includes a sleeve-shaped receiving portion that is configured to be connected to the bone anchor or to a bone anchor extension, and wherein the coupling body further includes an engagement structure configured to resiliently cooperate with an engagement structure on the bone anchor or the bone anchor extension to provide a connection between the coupling body and the bone anchor or the bone anchor extension. Preferably the engagement structure of the coupling body is formed by a separate engagement member that is urged via a biasing member into engagement with a recess provided in an outer surface of the bone anchor or bone anchor extension.

The coupling device according to this aspect is quickly and safely connectable to the bone anchor or bone anchor extensions, and also releasable easily after use. The coupling device is easily mountable to the extension sleeves and can be locked in one step and easily removed in one step.

The coupling device according to the foregoing aspects may be particularly useful for minimally invasive surgery (MIS), in which bone anchor extensions may provide a minimally invasive access to the vertebrae. However, the coupling device may also be applied during open surgery. While in spinal surgery, the coupling device can be applied in various correction steps, the application of the coupling device is not limited thereto. Rather, the coupling device may be employed in all kinds of orthopedic surgery where two bone implants have to be connected temporarily and where the connection should be adjustable in length and spatial orientation.

BRIEF DESCRIPTION OF THE DRAWINGS

Further features and advantages will become apparent from the description of embodiments by means of the accompanying drawings. In the drawings.

DETAILED DESCRIPTION

Figure 1:
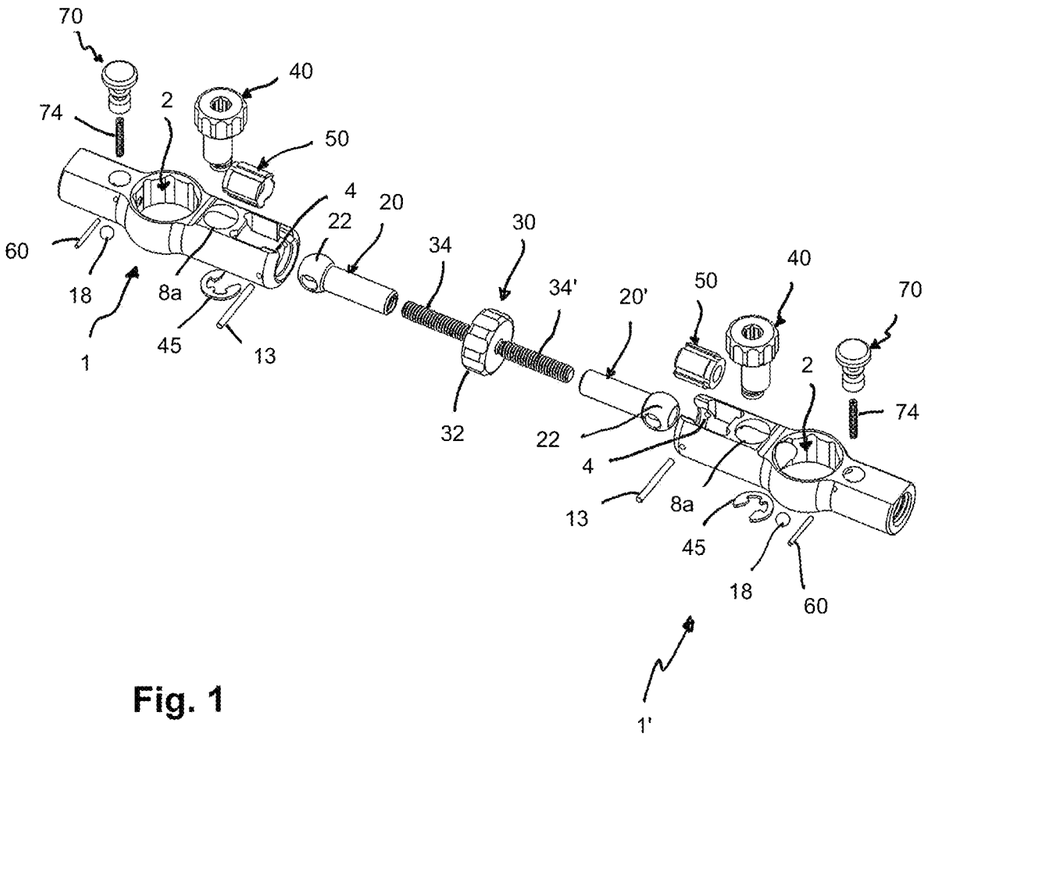
FIG. 1 shows a perspective exploded view of a coupling device according to an embodiment of the invention.
Figure 2:
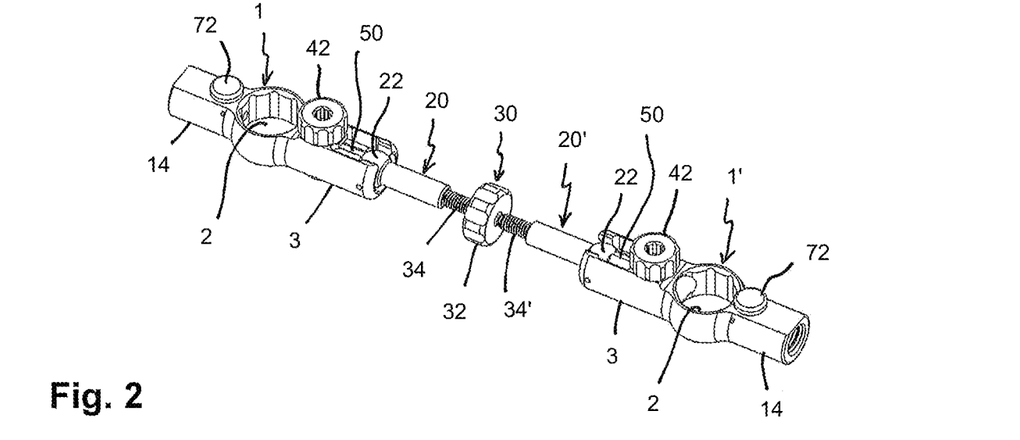
FIG. 2 shows a perspective view of the coupling device of FIG. 1 in an assembled state.
Figure 3:
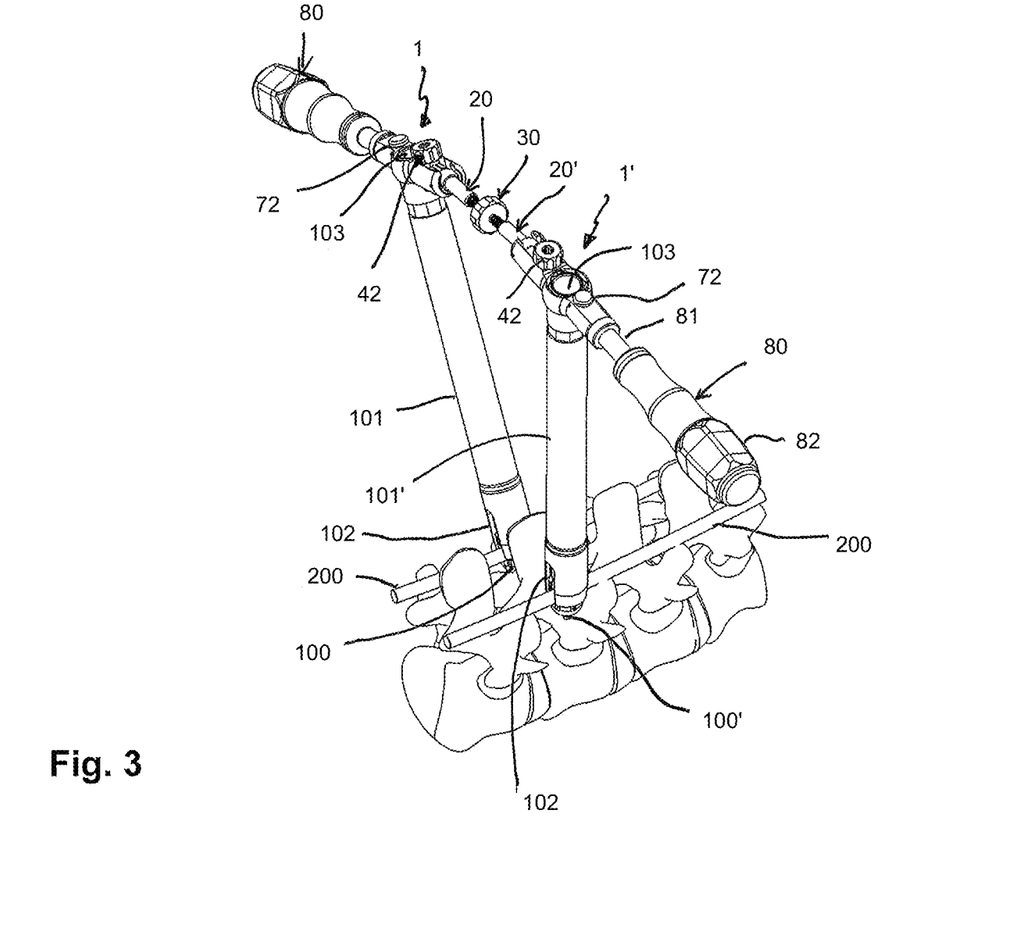
FIG. 3 shows a perspective view of the coupling device of FIGS. 1 and 2 attached to bone anchor extensions that are fixed to bone anchors inserted into pedicles of a vertebra.

Referring to FIGS. 1 to 3, a coupling device according to an embodiment of the invention includes a first coupling body 1 and a second coupling body 1' that are connected by a connection device that includes a first connection member 20, a second connection member 20', and a length adjustment member 30. The length adjustment member 30 is arranged between the first connection member 20 and the second connection member 20'. The first and second coupling bodies 1, 1' are configured to be connected to bone anchors 100, 100', respectively, via bone anchor extensions 101, 101'.

The bone anchors 100, 100' may have a shank for anchoring in bone and a head (not shown in detail). The bone anchors 100, 100' may be designed as polyaxial bone anchors, wherein the head is pivotably held in a receiving part that has a U-shaped recess for receiving a stabilization rod 200. The bone anchor extensions 101, 101' may be sleeve-shaped with an inverted U-shaped recess 102 to permit the rod 200 to be guided therethrough. In addition, the bone anchor extensions 101, 101' may be detachably mountable to the bone anchors 100, 100'. Preferably, the bone anchor extensions 101, 101' may have such a length that they extend out of a patient's skin, for example, in cases where minimally invasive surgery is being performed. In addition, the inner diameter of the bone anchor extensions 101, 101' may be such that instruments and/or parts of a bone anchor, for example a locking member, can be passed through to lock a polyaxial position of the bone anchor.

Figure 4:
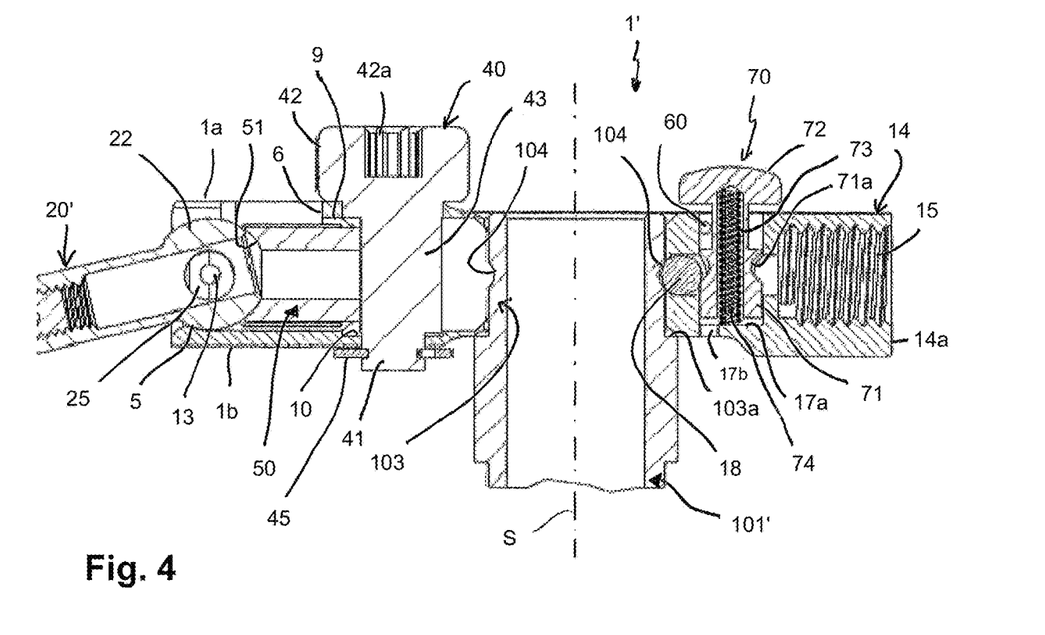
FIG. 4 shows a cross-sectional view of one part of the coupling device of FIGS. 1 to 3 attached to one bone anchor extension, wherein the cross-section is taken in a plane spanned by a central axis of a coupling body of the coupling device and a central axis of the bone anchor extension.
Figure 5:
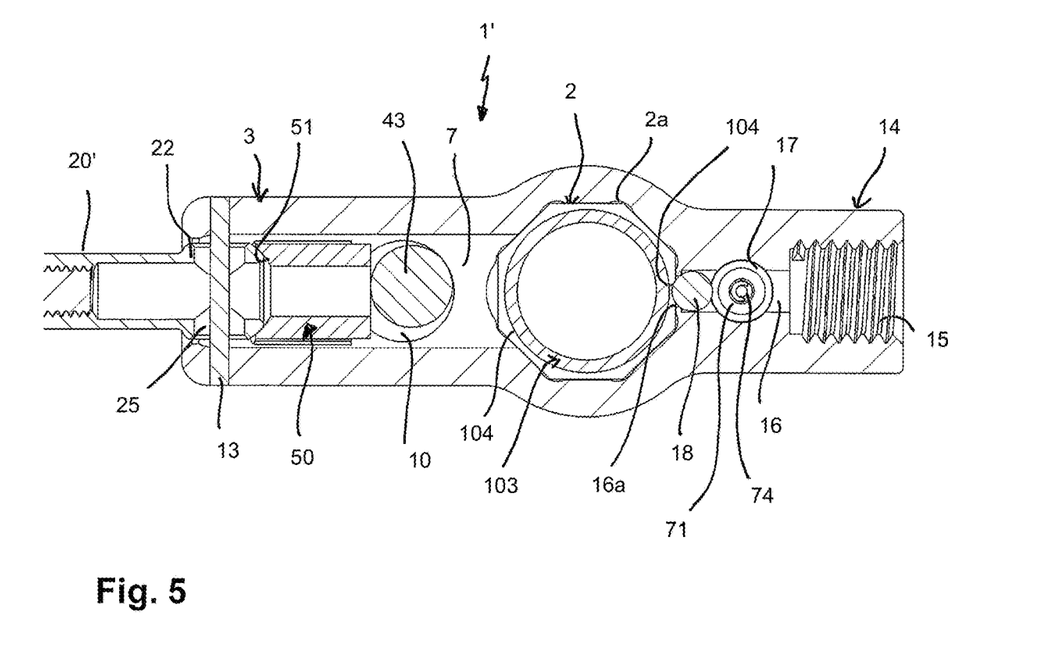
FIG. 5 shows a cross-sectional view of the part of the coupling device shown in FIG. 4, wherein the cross-section is taken in a plane containing the central axis of the coupling body and perpendicular to a central axis of the bone anchor extension.

As shown in greater detail in FIGS. 4 and 5, the first and second coupling bodies 1, 1' are configured to connect to free end portions 103 of the bone anchor extensions 101, 101'. The outer shape of the end portion 103 of the bone anchor extensions 101, 101' may have a polygonal contour, for example an octagonal contour. Furthermore, in the outer surface of the end portion 103, a circumferential groove 104 is formed, which functions as an engagement structure for a locking member for locking the connection between each of the bone anchor extensions 101, 101' and the first and second coupling bodies 1, 1', respectively. The circumferential groove 104 may have a substantially circular-segment shaped contour in a cross-sectional plane that extends radially from the sleeve axis s of the bone anchor extensions 101, 101'. Preferably, the groove 104 may be located in an axial direction approximately halfway between the free end and an annular step 103a.

As can further be seen in greater detail in FIGS. 6 to 9, each of the coupling bodies 1, 1' is a substantially elongate part having a top surface 1a and an opposite bottom surface 1b, and a sleeve-shaped opening 2 extending from the top surface 1a to the bottom surface 1b. The sleeve shaped-opening 2 is configured to fit onto the free end portion 103 of each of the bone anchor extensions 101, 101'. The first and the second coupling body are identical. As can be seen in particular in FIG. 4, the annular step 103a of the bone anchor extension forms an abutment for the first and second coupling body 1, 1' when placed onto the end portion 103 of the bone anchor extension 101, 101'. An inner wall defining the sleeve-shaped opening 2 has a polygonal inner contour, the edges or corners 2a of which may be rounded. Thereby, a form fit connection with the end portion 103 of the bone anchor extension 101, 101' can be established. The annular step 103a may be at such a distance from the free end of the bone anchor extension 101, 101' that in the mounted state of the coupling body 1, 1', the free end of the bone anchor extension 101, 101' and the coupling body 1, 1' are substantially flush with each other. An outer contour of the first and second coupling body 1, 1' in the region of the sleeve-shaped opening 2 may be spherical segment-shaped, or otherwise rounded, or may have any other shape.

From the sleeve-shaped opening 2, a first or inner arm 3 extends to one side in a direction perpendicular to the sleeve axis s. It shall be noted that in the mounted state, the sleeve axis s of the bone anchor extension and that of the sleeve shaped opening are coaxial, and the top surface 1a faces away from the direction in which the bone anchor extension extends from the coupling bodies 1, 1'. The inner arm 3 has a free outer end 3a that faces toward the respective other one of the first and second coupling bodies 1, 1'. A hollow passage 7 extends completely through the arm 3 from the sleeve-shaped opening 2 towards the free end 3a in a direction perpendicular to the sleeve axis s. Adjacent to the free end 3a in the passage, a receiving portion 4 for accommodating an end portion 22 of the connection member 20, 20' is provided. The receiving portion 4 has a support surface 5 that is shaped so as to allow a pivoting movement of an end portion 22 of the connection member 20, 20', which is described in greater detail below. In the example shown, the support surface 5 has a spherical shape that cooperates with a ball-shaped end portion 22 of the connection member 20, 20'. However, any other surface, e.g., a conically tapering surface that allows a pivoting movement may be also provided. In the top surface 1a of the inner arm 3, a cut-out 6 is formed that provides access to the receiving portion 4. The cut-out 6 has a narrower portion 6a adjacent to the free end 3a which is narrower than a width of the end portion 22 of the connection member 20, 20', so that the end portion 22 can neither be inserted at the narrower portion 6a nor be removed through the free end 3a. Hence, the end portion of the connection member 20, 20' can be pivotably captured in the receiving portion 4. The cut-out 6 further includes a widened portion 6b with substantially flat side walls that has a width greater than a maximum width of the end portion 22 of the connection member 20, 20' and that permits insertion of the end portion 22 into the receiving portion 4.

Figures 6, 7:
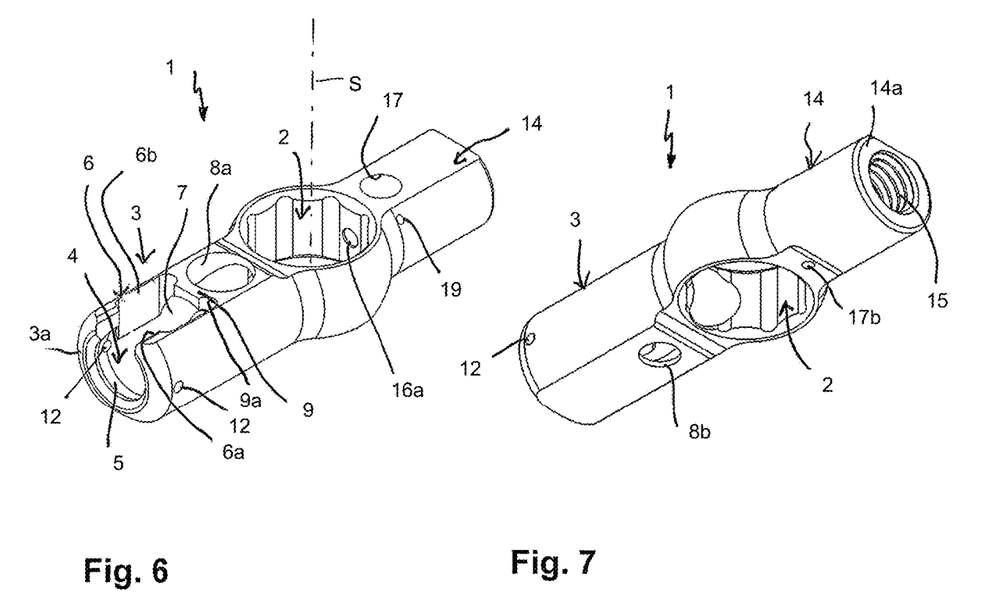
FIG. 6 shows a perspective view from the top of a coupling body of the coupling device according to FIGS. 1 to 5.
FIG. 7 shows a perspective view from the bottom of the coupling body of FIG. 6.

At a position between the receiving portion 4 and the sleeve-shaped opening 2, an upper opening 8a and a lower opening 8b having a smaller width than the upper opening 8a are provided in the top surface 1a and the bottom surface 1b, respectively. The openings 8a, 8b are preferably circular and serve to accommodate a locking member 40 for locking the pivot position of the connection member 20, 20' in the receiving portion 4, explained in greater detail below. Moreover, as shown in FIGS. 4 and 6, the passage 7 is configured to accommodate a pressure member 50 that serves for transferring pressure from the locking member 40 onto the end portion 22 of the connection member 20, 20'. Between the upper opening 8a and the cut-out 6, a small roof 9 is formed by the top surface 1a of the inner arm 3, that is configured to cover a portion of the pressure member 50. Therefore, in the mounted state as shown in FIG. 4, the pressure member 50 cannot escape from the inner arm 3. In the roof 9 and the sidewalls of the arm 3, further cut-outs 9a may be provided to provide space for the insertion of the pressure member 50. Above the opening 8b, a recess 10 may be formed in the inner wall of the inner arm 3 that allows a portion of the locking member 40 to extend therein.

Figures 8, 9:
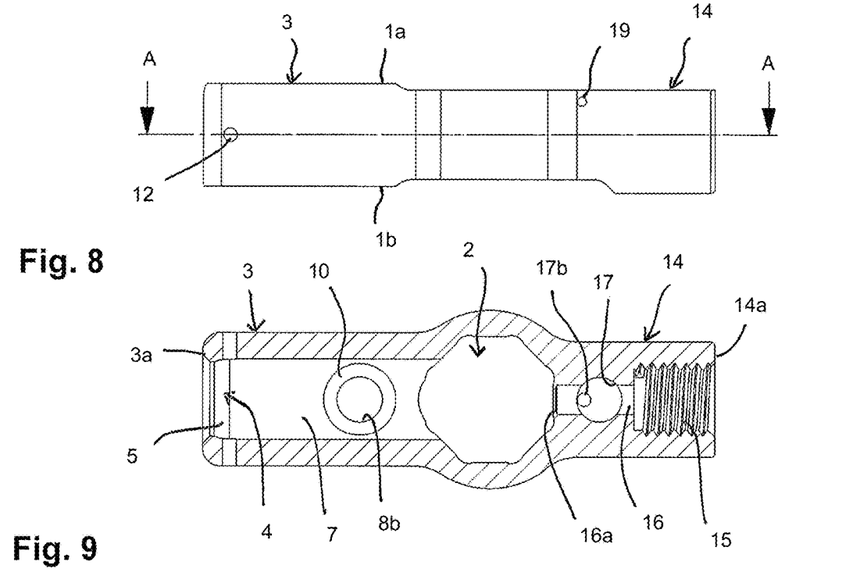
FIG. 8 shows a side-view of the coupling body of FIGS. 6 and 7.
FIG. 9 shows a cross-sectional view of the coupling body of FIGS. 6 to 8, the cross-section taken along line A-A in FIG. 8.

As can be seen in FIGS. 6 to 8, the top surface 1a and the bottom surface 1b of the coupling body may be flat at a position of the inner arm 3, and the inner arm 3 may have a height that is greater than a height of the portion with the sleeve-shaped opening 2. An outer side wall of the inner arm 3 between the top surface 1a and the bottom surface 1b may be cylindrically shaped. Moreover, close to the free end 3a, there are pin holes 12 provided on opposite sides of the cut-out 6 that extend perpendicular to the sleeve axis s. The pin holes 12 serve for receiving a pin 13 (FIG. 5) therein that may extend through the end portion 22 of the connection member 20, 20', for securing the end portion 22 in the receiving portion 4.

On the side of the sleeve-shaped opening 2 opposite to the inner arm 3 a second or outer arm 14 is formed. A longitudinal axis of the outer arm 14 is substantially perpendicular to the sleeve axis s and may be coaxial with a longitudinal axis of the inner arm 3. The outer arm 14 has a free end 14a from which a threaded bore 15 that is coaxial with the longitudinal axis of the outer arm 14 extends to a distance from the free end 14a. Between a bottom of the coaxial threaded bore 15 and the sleeve-shaped opening 2, a further coaxial bore 16 is provided that has a smaller width than the coaxial threaded bore 15. The coaxial bore 16 is connected through an opening 16a with the sleeve-shaped opening 2. The opening 16a has a smaller width than the coaxial bore 16. Approximately halfway between the opening 16a and the bottom of the coaxial threaded bore 15, a cylindrical bore 17 is provided that extends perpendicularly to the longitudinal axis of the outer arm 14, from the top surface 1a to a distance from the bottom surface 1b. At a side closer to the sleeve-shaped opening 2, a further smaller bore 17b is provided that is open to the bottom surface 1b. The bore 17b may, e.g., facilitate a cleaning process of the device.

Adjacent to the opening 16a, the coaxial bore 16 serves for accommodating a ball 18, a diameter of which is such that the ball can slide in the bore 16 and extend partially through the opening 16a. Moreover, a pin hole 19 is formed in one side of the outer arm 14 in a direction perpendicular to the sleeve axis s and at a height between the top surface 1a and the coaxial bore 16. The pin hole 19 is located in the region of the coaxial bore 17, so that a pin 60 that is placed in the pin hole 19 extends into the bore 17. The pin 60 may serve as a securing device for preventing an actuating member 70 provided in the bore 17 from being removed inadvertently.

The actuating member 70 includes a first cylindrical portion 71 that can slide in the bore 17 and an actuating knob 72 that extends out from the top surface 1a and has a greater width than the bore 17. The first cylindrical portion 71 has in its outer surface a circumferential groove 71a that is sized to allow a portion of the ball 18 to be received therein. Between the first cylindrical portion 71 and the actuating knob 72, a reduced diameter neck 73 may be provided. Inside the actuating member 70, there is a coaxial cylindrical bore that receives a biasing member, such as a helical spring 74. In the mounted state shown for example in FIG. 4, the biasing member urges the actuating knob 72 away from the top surface 1a, such that the first cylindrical portion 71 urges the ball 18 into the opening 16a, where it can extend into the groove 104 of the end portion 103. Once the ball 18 engages the groove 104, the coupling body 1, 1' is locked in an axial direction relative to the bone anchor extension 101, 101'. Pushing the actuating knob 72 toward the bottom surface 1b results in a compression of the spring 74, such that the ball 18 can wander into the groove 71a of the cylindrical portion 71. By means of this, the locking is released. Hence, the ball 18 actuated with the aid of a biasing member forms an engagement structure that resiliently cooperates with an engagement structure at the bone anchor extension.

Like the inner arm 3, the outer arm 14 may have cylindrical side surfaces between the top and the bottom surfaces. The bottom surface 1b may have a step that widens towards the free end 14a.

Figure 10:
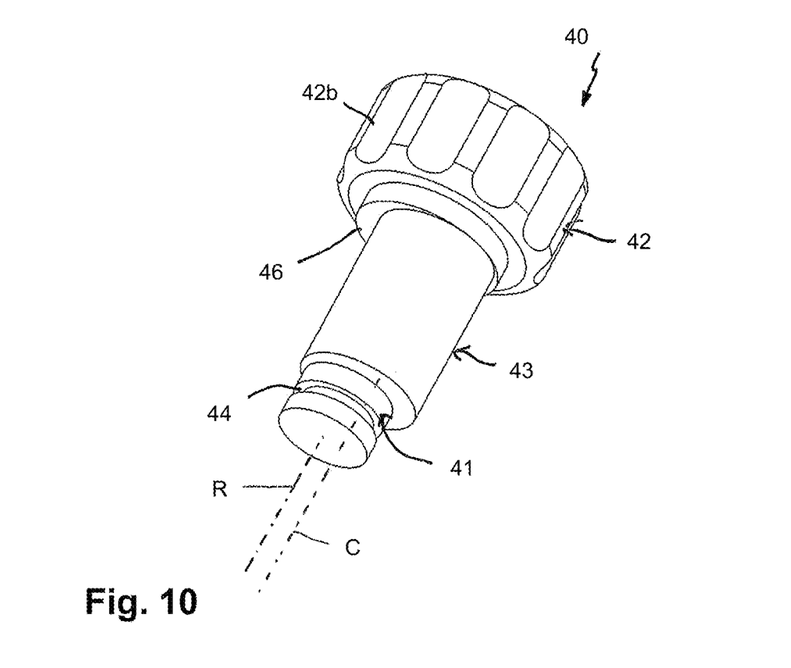
FIG. 10 shows a perspective view of a locking member for locking a pivot position of a connection member relative to a coupling body in the coupling device of FIGS. 1 to 5.

As depicted in greater detail in FIG. 10, the locking member 40 is formed as an eccentric or otherwise asymmetric device. The locking member 40 includes a substantially cylindrical shaft 41 that defines an axis of rotation R, wherein the shaft 41 is rotated via a rotation knob 42 or rotation wheel. Between the rotation knob 42 and the shaft 41, a cylindrical eccentric portion 43 is provided, the cylinder axis c of which is parallel to the axis of rotation R. Hence, when rotating the shaft 41 with the knob 42, the cylinder axis c of the eccentric portion 43 rotates around the axis of rotation R of the shaft 41. In other embodiments, any portion with a variable width relative to the axis of rotation R, for example, a portion that is rotationally asymmetric relative to the axis of rotation R, can also be implemented. At a distance from the free end of the shaft 41, a groove 44 is formed that serves for receiving a securing clip 45. Between the eccentric portion 43 and the actuating knob 42, a disk-shaped projection 46 with an outer diameter that is smaller than that of the knob 42 and greater than that of the eccentric portion 43 may be provided. The locking member 40 has a size such that when it is mounted to the inner arm 3, the eccentric portion 43 extends through the passage 7 and the shaft 41 with the groove 44 extends through the lower opening 8b. When the locking member 40 is mounted to the inner arm 3, the disk-shaped projection 46 may rest on or next to the roof 9, and the knob 42 extends above the top surface 1a. Hence, the knob 42 of the locking member 40 and the knob 72 of the actuating member 70 both protrude above the top surface 1a. This facilitates easier handling of the device. In the mounted state, the eccentric portion 43 can extend at its lower side into the recess 10. Once the securing clip 45 is provided in the groove 44, the locking member 40 is rotatably held in the inner arm 3.

In the free end surface of the rotating knob 42, an engagement recess 42a may be formed for actuating the locking member 40 with a driver, for example. Alternatively, the knob 42 can be rotated by hand using a gripping structure 42b, for example, longitudinal grooves.

Figure 11:
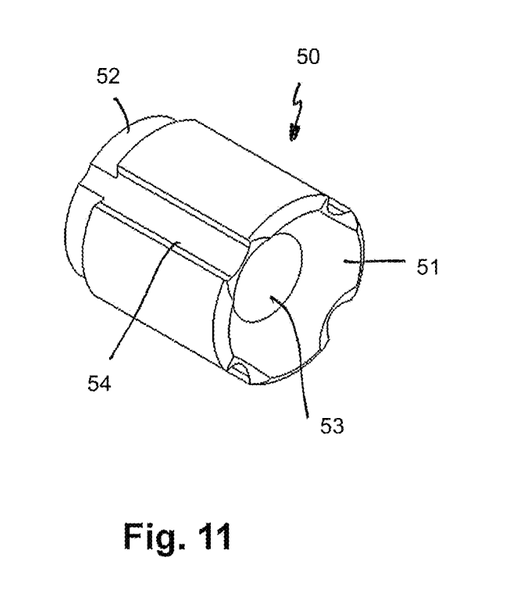
FIG. 11 shows a perspective view from the front of a pressure member for locking a pivot position of the coupling device of FIGS. 1 to 5.
Figure 12:
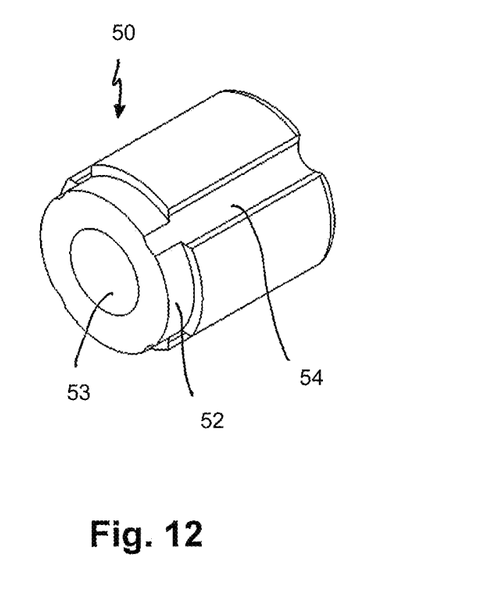
FIG. 12 shows a perspective view from the rear of the pressure member of FIG. 11.

The pressure member 50 is shown in greater detail in FIGS. 11 and 12. The pressure member 50 is a substantially cylindrical part with an outer diameter that permits it to slide within the passage 7 and under the roof 9. At one free end a substantially spherically-shaped recess 51 is formed that matches the outer shape of the end portion 22 of the connection member 20, 20'. By means of this, pressure can be distributed onto the end portion 22. At the other free end opposite to the spherically-shaped recess 51, a reduced diameter section 52 may be provided that may have a function of facilitating insertion of the pressure member 50 into the passage 7. A coaxial bore 53 may extend completely through the pressure member 50 from one end to the opposite end. Moreover, longitudinal grooves 54 may be formed in the outer surface of the pressure member 50 to facilitate cleaning. The pressure member 50 has an axial length such that it fills the space between the locking member 40 and the end portion 22 of the connection members 20, 20' when inserted into the inner arm 3, in such a manner that the spherically-shaped recess 51 contacts the end portion 22 of the connection member 20, 20'.

Figure 13:
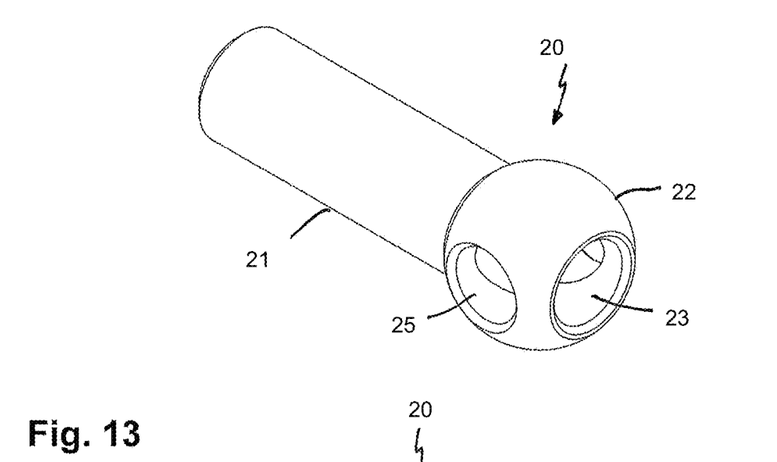
FIG. 13 shows a perspective view from the front of a connection member of the coupling device of FIGS. 1 to 5.
Figure 14:
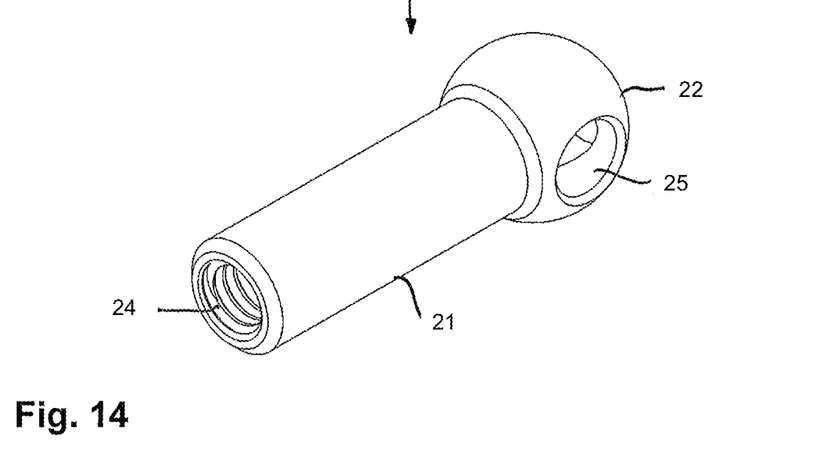
FIG. 14 shows a perspective view from the rear of the connection member of FIG. 13.
Figure 15:
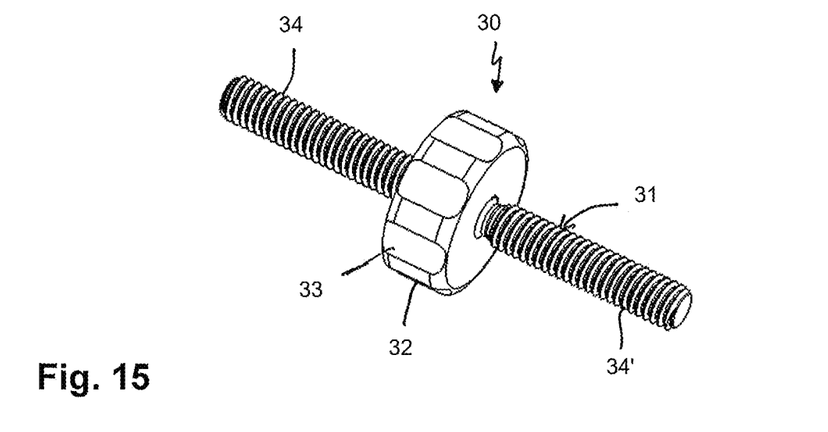
FIG. 15 shows a perspective view of a length adjustment member that is part of the coupling device of FIGS. 1 to 5.

Next, with further reference to FIGS. 13 and 14, the connection members 20, 20' will be described. Each of the connection members 20, 20' includes a cylindrical shaft portion 21 and a ball-shaped end portion 22. An outer diameter of the ball-shaped end portion 22 may be greater than the outer diameter of the shaft 21, and furthermore, may be such that the ball-shaped end portion 22 can be pivotably held in the receiving portion 4 of the inner arm 3. The connection member 20, 20' may have a longitudinal passage 23 that extends through the connection member completely from the free end of the shaft 21 through the end portion 22. Adjacent to the free end of the shaft 21, the passage 23 includes an internal thread 24, 24' over an axial length of the shaft 21 that permits adjustments to a distance between the connection members 20, 20' to a necessary extent, for example, by using the length adjustment member 30. The respective thread directions of the internal threads 24, 24' is different for the first connection member 20 and the second connection member 20'. For example, the internal thread 24 of the first connection member 20 may be a right-hand thread and the internal thread 24' of the second connection member 20' may be a left-hand thread. In addition, transverse holes 25 are provided on opposite sides of the ball-shaped end portion 22 and are arranged perpendicularly to the longitudinal passage 23. The holes 25 may taper towards a center of the ball-shaped end portion 22. When the ball-shaped end portion 22 is received in the receiving portion 4 of the inner arm 3, the pin 13 can extend through the pin holes 12 of the inner arm 3 and through the transverse holes 25. Due to the tapered shape, the ball-shaped end portion 22 can pivot in the receiving portion 4 until the pin 13 abuts against the tapered wall of the transverse holes 25. Hence, the holes 25 with the pin 13 are configured to limit the pivoting movement of the ball-shaped end portion 22 in the receiving portion 4.

The length adjustment member 30, as depicted in FIGS. 1 to 3 and 15, includes a shaft 31. At the center of the shaft 31 in a longitudinal direction of the shaft axis, an actuating knob 32 or wheel is provided that can be gripped by hand and that preferably has a gripping structure 33, for example, longitudinal grooves. On each of the shaft portions extending to the right side and to the left side from the actuating knob 32, an external thread 34, 34' is provided that is configured to cooperate with the respective internal threads 24, 24' of the connection members 20, 20'. When the length adjustment member 30 is mounted between the first connection member 20 and the second connection member 20', the shaft axis of the shaft 31 defines a connection axis between the length adjustment member 30 and the connection members 20, 20'.

Optionally, as depicted in FIG. 3, a handle 80 can be mounted to each of the outer arms 14 of the first and second coupling bodies 1, 1'. The handle 80 may have a threaded shaft 81 that can be screwed into the threaded hole 15 of the outer arm 14, and a grip portion 82. The handle 80 is not essential for the functioning of the coupling device but may be used during a surgical correction step.

The pressure member 50 and the connection member 20, 20' may be mounted to the inner arm 3 of the coupling bodies 1, 1', one after the other, by inserting them through the widened portion 6b of the cutout 6.

The parts and portions of the coupling device may be made of any material, preferably, however of bio-compatible materials, for example of titanium or stainless steel, of a bio-compatible alloy, such as NiTi-alloys, for example Nitinol, of magnesium or magnesium alloys, or of a bio-compatible plastic material, such as, for example polyether ether ketone (PEEK) or poly-L-lactide acid (PLLA). In addition, the parts can be made of the same material as or of different materials from one another.

In operation, the coupling device is placed on the bone anchor extensions 101, 101' that are fixed to bone anchors 100, 100'. The bone anchors 100, 100' may be, for example, pedicle screws. The coupling device is usually preassembled. Before placing the coupling device onto the bone anchor extensions 101, 101', the connection members 20, 20' are in the pivotable configuration. When placing the coupling bodies 1, 1' with the sleeve-shaped openings 2 onto the bone anchor extensions 101, 101', respectively, the actuating button 72 is pushed down to release the ball 18 so that the ball 18 does not protrude through the opening 16a. The first and the second coupling bodies 1, 1' are placed onto the end portions 103 of the bone anchor extensions 101, 101', respectively. During this step, the ball 18 snaps into the groove 104 of the end portion 103. Moreover, the form fit connection between the end portion 103 of the bone anchor extension and the sleeve-shaped opening 2 due to the complementary polygonal shapes secures the coupling bodies 1, 1' against rotation relative to the bone anchor extensions. Then the button 72 is released so that the ball 18 is pressed into the groove 104, thereby locking the first and second coupling bodies 1, 1' to the bone anchor extensions 101, 101'. Since the end portions 22 of the connection members 20, 20' can pivot in the receiving portions 4 of the coupling bodies 1, 1', the coupling device can be adapted to the position of the bone anchor extensions 101, 101' in the spatial directions.

The length of the coupling device can be adjusted by rotating the actuating knob 32 of the length adjustment member 30. Rotating the knob 32 in one direction increases the distance between the connection members 20, 20'. Rotating the knob 32 in the opposite direction decreases the distance between the connection members 20, 20'. Hence, the length of the coupling device can be adjusted with only one hand of a user holding and rotating the knob 32.

Once the coupling device is placed onto the bone anchor extensions and the distance between the connection members 20, 20' has been adjusted, the pivot position of the connection members 20, 20' can be locked using the locking member 40. As shown in FIG. 5, the eccentric portion 43 of the locking member 40 has a first position where it is farthest away from the pressure member 50 (or more generally from the free end 3a of the inner arm 3), so that the eccentric portion 43 cannot exert sufficient pressure onto the pressure member to lock the end portion 22. By rotating the actuating knob 42 of the locking member, the eccentric portion 43 presses onto the pressure member 50, so that when the eccentric portion 43 faces or is at a closest position to the pressure member 50 (or more generally to the free end 3a of the inner arm 3), sufficient pressure is exerted onto the end portion 22 to lock the pivot position of the connection member 20, 20'. Locking and releasing of the connection members 20, 20' can be effected by rotating the locking member in one direction or in the opposite direction.

Finally, a desired correction step can be carried out. This can be, for example, a step of rotating the vertebra relative to other vertebrae. The handles 80 may be used to more easily perform this step.

In a further development, at least two or more coupling devices may be mounted to bone anchor extensions on adjacent vertebrae and coupled by additional connectors, so that the coupling devices form an assemblage. By means of this, more than one vertebra can be corrected or otherwise adjusted simultaneously together.

Other modifications of the coupling device may also be conceivable. It shall be noted that the length adjustment of the coupling device may be realized using another advancement structure that permits both increasing and decreasing the distance between the connection members. Also, the specific shapes of the various parts of the coupling device are not limited to the shapes as explained in connection with the above embodiment. Deviations may be possible. The optional handles may also be attached to the coupling device and fixed thereto by any other means.

The bone anchor extension may be part of the bone anchor itself, for example, in the form of extended legs of a receiving part of a polyaxial bone anchor that can be broken away after the correction steps have been performed. Hence, the invention also relates to a system including the coupling device and bone anchors and corresponding bone anchor extensions.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling device for use in orthopedic surgery comprising:
a first coupling body configured to be coupled to a first bone anchor;
a second coupling body configured to be coupled a second bone anchor; and
a connection device configured to connect the first coupling body to the second coupling body, the connection device comprising a first connection member connectable to the first coupling body, a second connection member connectable to the second coupling body, and a length adjustment member positionable between and insertable at least partially into each of the first and second connection members;
wherein each of the first and second connection members is movable relative to the length adjustment member along a connection axis, and wherein the length adjustment member is configured to be actuated in a first direction to increase a distance between the first connection member and the second connection member along the connection axis, and is configured to be actuated in a second direction that is different from the first direction to decrease the distance between the first connection member and the second connection member along the connection axis.

2. The coupling device of claim 1, wherein the first and second connection members each comprises an advancement structure for gradually adjusting the distance between the first and second connection members along the connection axis.

3. The coupling device of claim 2, wherein the length adjustment member comprises advancement structures configured to mate respectively with the advancement structures of the first and second connection members.

4. The coupling device of claim 3, wherein the advancement structures of the first and second connection members and of the length adjustment member comprise threads.

5. The coupling device of claim 1, wherein the length adjustment member comprises a first extension comprising a right-hand thread configured to cooperate with the first connection member and a second extension comprising a left-hand thread configured to cooperate with the second connection member, such that the distance between the first and second connection members along the connection axis increases when the length adjustment member is rotated in the first direction, and the distance between the first and second connection members along the connection axis decreases when the length adjustment member is rotated in the second direction.

6. The coupling device of claim 1, wherein at least one of the first or second connection members is configured to pivot with respect to the coupling body to which it is connected.

7. The coupling device of claim 6, wherein the coupling body to which the at least one connection member is connected comprises a receiving portion configured to pivotably receive an end portion of the at least one connection member.

8. The coupling device of claim 6, wherein at least one of a pressure member or a locking member is configured to lock and release a pivot position of the at least one connection member relative to the coupling body to which it is connected.

9. The coupling device of claim 8, wherein the locking member comprises an asymmetric portion for locking and releasing the pivot position of the at least one connection member relative to the coupling body to which it is connected.

10. The coupling device of claim 1, wherein each of the first and second coupling bodies defines a sleeve shaped opening for coupling the coupling body to a bone anchor or a bone anchor extension.

11. The coupling device of claim 10, wherein at least one of the first or second coupling bodies comprises an engagement structure configured to resiliently cooperate with an engagement structure on a bone anchor or a bone anchor extension to facilitate a connection between the at least one coupling body and the bone anchor or bone anchor extension.

12. The coupling device of claim 11, wherein the engagement structure of the at least one coupling body comprises a separate engagement member configured to be urged by a biasing member into engagement with a recess provided at an outer surface of the bone anchor or bone anchor extension.

13. The coupling device of claim 1, wherein at least one of the first or second coupling bodies comprises a bone anchor extension that extends away from the at least one of the first or second coupling bodies to connect to a bone anchor.

14. The coupling device of claim 13, wherein the bone anchor extension is releasable from the at least one of the first or second coupling bodies.

15. A coupling device for use in orthopedic surgery comprising:
a coupling body configured to be coupled to a bone anchor;
a connection member pivotably connected to the coupling body; and
a locking member configured to act directly or indirectly on the connection member to lock a pivot position between the connection member and the coupling body;
wherein the locking member comprises an asymmetric portion configured to assume a first configuration where the pivot position is locked and to assume a second configuration where the pivot position is released, and wherein the locking member is rotatable to adjust the asymmetric portion between the first and second configurations.

16. The coupling device of claim 15, wherein the asymmetric portion comprises an eccentric portion that is offset relative to an axis of rotation of the locking member.

17. The coupling device of claim 15, further comprising a pressure member configured to exert pressure on the connection member to lock the pivot position, and wherein the asymmetric portion is configured to act on the pressure member.

18. The coupling device of claim 15, wherein the connection member defines a connection axis, and wherein an axis of rotation of the locking member is transverse to the connection axis.

19. A tool comprising:
a first coupling device and a second coupling device according to claim 15; and
a length adjustment member positioned between and configured to adjust a distance between the first and second coupling devices.

20. A coupling device for use in orthopedic surgery comprising:
a connection member; and
a coupling body pivotably connected to the connection member, the coupling body comprising:
a sleeve-shaped receiving portion connectable to a bone anchor or to a bone anchor extension;
an engagement structure configured to extend into the sleeve-shaped receiving portion to cooperate with a corresponding engagement structure on the bone anchor or bone anchor extension to connect the coupling body to the bone anchor or bone anchor extension; and
a separate biasing member configured to urge the engagement structure into the sleeve-shaped receiving portion to engage the corresponding engagement structure on the bone anchor or bone anchor extension.

21. The coupling device of claim 20, wherein the engagement structure comprises an engagement member that is separate from the sleeve-shaped receiving portion and the biasing member.

22. A tool comprising:
a first coupling device and a second coupling device according to claim 20; and
a length adjustment member positioned between and configured to adjust a distance between the first and second coupling device.

* * * * *